(12) United States Patent
Di Pasquale et al.

(10) Patent No.: US 9,290,815 B2
(45) Date of Patent: *Mar. 22, 2016

(54) METHOD FOR QUANTIFYING HUMAN DNA (75) Inventors: Francesca Di Pasquale, Hilden (DE); Holger Engel, Hilden (DE)

(73) Assignee: Qiagen GMBH, Hilden (DE)

( * ) Notice: Subject to any disclaimer, the term of this patent is extended or adjusted under 35 U.S.C. 154(b) by 38 days.

This patent is subject to a terminal disclaimer.

(21) Appl. No.: 14/000,096

(22) PCT Filed: Feb. 21, 2012

(86) PCT No.: PCT/EP2012/052913
§ 371 (c)(1),
(2), (4) Date: Dec. 13, 2013

(87) PCT Pub. No.: WO2012/113780
PCT Pub. Date: Aug. 30, 2012

(65) Prior Publication Data
US 2014/0234834 A1 Aug. 21, 2014

(30) Foreign Application Priority Data
Feb. 21, 2011 (EP) .................................... 11155164

(51) Int. Cl.
*C12Q 1/68* (2006.01)

(52) U.S. Cl.
CPC ............ *C12Q 1/6888* (2013.01); *C12Q 1/6851* (2013.01); *C12Q 1/6876* (2013.01); *C12Q 2600/166* (2013.01)

(58) Field of Classification Search
None
See application file for complete search history.

(56) References Cited

U.S. PATENT DOCUMENTS

| 4,458,006 A | 7/1984 | Donges et al. |
| 7,662,594 B2 | 2/2010 | Kong et al. |
| 2004/0209298 A1 | 10/2004 | Kamberov et al. |
| 2009/0017453 A1 | 1/2009 | Maples et al. |
| 2010/0035232 A1 | 2/2010 | Ecker et al. |

OTHER PUBLICATIONS

Arriola Edurne et al.: Evaluation of Phl29-based whole-genome amplification for microarray-based comparative genomic hybridisation; Laboratory Investigation, vol. 87, No. 1, Jan. 2007, pp. 75-83.
Renard A et al.: Application of whole genome amplification and quantitaive PCR for detection and quantification of spoilage yeasts in orange juice; International Journal of Food Microbiology; vol. 126, No. 1-2; pp. 195-201; 2008.
Hansen, Helen M. et al.: DNA quantification of whole genome amplified samples for genotyping on a multiplexed bead array platform; vol. 16, No. 8, Aug. 2007; pp. 1686-1690.
Walker J. A. et al.: Multiplex polymerase chain reaction for simulataneous quantitation of human, nuclear, mitochondrial, and male Y-chromosome DNA: application in human identification; Analytical biochemistry, vol. 337, No. 1, pp. 89-97; 2005.
Hanson Erin K. et al; Whole genome amplification strategy for forensic genetic analysis using single or few cell equivalents of genomic DNA; Analytical Biochemistry, vol. 346, No. 2, Nov. 2005; pp. 246-257.
Vallone P. M. et al.: Development and usage of a NIST standard reference material for real time PCR quantitation of human DNA; Forensic Science International: Genetics Supplement Series; vol. 1 No. 1, Aug. 1, 2008, pp. 80-82.
Lovmar L. et al.: Quantitative evaluation by minisequencing and mlrcoarrays reveals accurate multiplexed SNP genotyping of whole genome amplified DNA; Nucleic Acids Research, vol. 31, No. 21, Jan. 1, 2003; pp. (E129)1-(E129)9.
Chia Dennis J. et al.: Distinct Alterations in chromatine organization of the two IGF-I promoters precede growth hormone-induced activation of IGP-I gene transcription; Molecular Endocrinology; vol. 24, No. 4, Apr. 2010; pp. 779-789.
Ellison et al.: Routes to improving the reliability of low level DNA analysis using real-time PCR; BMC Biotechnology 6: 33, 2006.
Official Journal of the European Union, L 50, pp. 28-43; 2004.
Zahng et al.: Whole genome amplification from a single cell: Implications for genetic analysis; Proc. Natl. Acad. Sci. 1992, 89:5847-5851.
Blanco et al.: Highly Efficient DNA synthesis by the Phage ø29 DNA Poiymerase; 1989; J. Biol, Chem. 264: 8935-40.
Dean et al.: Comprehensive human genome amplification using multiple displacement amplification; 2002; Proc. Natl. Acad. Sci; USA; 99(8): 5261-5266.
Vincent et al.: Helicase-dependent isothermal DNA amplification; 2004; EMBO rep. 5(8): 795-800.
An et al,: Characterization of a thermostable UvrD helicase and its participation in helicase dependent amplification; 2005; J. Biol. Chem.; 2005; vol. 280, No. 32; pp. 28952-28958.
Walker et al,: Strand displacement amplification—an isothermal, in vitro DNA amplification technique; 1992; Nucleic Acids Res, 20(7): 1691-6.
Liu et al.: Rolling Circle DNA synthesis: Small Circular Oligonucleotides as Efficient Templates for DNA Polymerases; 1996, J. Am. Chem. Soc.; 118:1587-1594.
Wang et al.: DNA amplification method tolerant to sample degradation; 2004; Genome Research 14: 2357-2366.
Dafforn et al.: Linear mRNA amplification from as little as 5 ng total RNA for global gene expression analysis; 2004; Biotechniques 37(5): 854-7.
Vuorinen et al.: Direct Detection of *Mycobacterium tuberculosis* Complex in Respiratory Specimens by Gen-Probe Amplified *Mycobacterium tuberculosis* Direct Test and Roche Amplicor *Mycobacterium tuberculosis* Test; J. Clin. Microbiol. 33: 1856-1859; 1995.

(Continued)

*Primary Examiner* — Samuel Woolwine
*Assistant Examiner* — Olayinka Oyeyemi
(74) *Attorney, Agent, or Firm* — Fanelli Haag PLLC (57) ABSTRACT

The invention provides for a method for quantifying one or more nucleic acids of a genome in a sample comprising the steps of, (a) amplifying a first nucleic acid to be quantified, (b) determining the amount of said first nucleic acid by comparison of the amount of amplification product from said first nucleic acid with at least one amplification product from a second template nucleic acid, (c) wherein said second template nucleic acid was generated using whole genome amplification and wherein the starting concentration of the second template nucleic acid is known.

25 Claims, 5 Drawing Sheets

(56) References Cited

OTHER PUBLICATIONS

Van Ness et al.: Isothermal reactions for the amplification of oligonucleotides; 2003; Prox. Natl. Acad. Sci: USA; 100(8): 4504-4509.

Notomi et al.: Loop-mediated isothermal amplification of DNA; 2000; Nucleic Acids Res. 28(12):e63.

Piepenburg et al.: DNA Detection Using Recombination Proteins; 2006; PloS Biol. 4(7): 1115-1120.

Karlin et al.: Applications and statistics for multiple high-scoring segments in molecular sequences; Proc. Natl. Acad. Sci. USA 1993; 90: 5873-5877.

Altschul et al.: Basic Local Alignment Search Tool; J. Mo. Biol. 1990; 215: 403-410.

Wilson: Inhibition and Facilitation of Nucleic Acid Amplification; Applied and Environmental Microbiology, Oct. 1997, pp. 3741-3751.

| SEQ ID NO. 1 target sequence | 5'-<br>TCAACAGGCCACCGTGAGGGAGGAGCTGGGCCGCACGCGGGCTGCTGG<br>GAGGCAGGCAGGGACTTGGCCCCGAGAGGCCGCCGTGGGGGCAAGAGC<br>TGGGCCTGGAGAGGCCCCTGGGAGGCAAGGGCGGGGCCTGCAGAGGCT<br>GTTCTCCAACCAGTGCTAGAACTGTACAGGCCACCAGGAGGCAGGAGG<br>TGGGCCCTCAGAGCTTGGCTGGAGAAAGTTCGGGGCCTACAAAGGCGG<br>TTGGGAGCTGGGCAGGAGTTGAGCCAAAAGAGCTTGCTTACTTGCTGG<br>GAGGCAGGGCCGGGAGAGCCCGACTTCAGGACAACTTGGGCCTGCGGC<br>AGTCGCCGGGAGGCCCAACCTTGGCGTGGAGGAGCCCACCGACCGGAG<br>ACCATTTGGGGCCTGGAGATGCCATCGGAGGGCAGGAGCTCATCCTGG<br>AGAGGCCACCGTGAGGCCTGACCTGGGCCTGGGGAGCTTGGCTTGAGG<br>AAGCTGTGGGCCGACCAAGGCCGCCAGGAGATGGGTAGGCACTGAGTC<br>CAAAGAGGTTGTTGAGAGGCAGGAATCGGGCCTGGAGACCCAACCAGG<br>AAGAAGAGCTGGGCCCGGAGAGAATGCACGGAGGGTGCA<u>AGTGGGTCT<br>GGAGAGGCCGACTTGAGGAGGTTCTGGGCCCGGAGAGGCCGCCGGAAG<br>GGAAAAACTGGGCCTGGAAAGGCCGTTGTCAGGAATGAGCCCCATGGG<br>CCTGAAGAGGCCACTGGCAGGCGGGAGCTGGGCCTGCCGAAGCGGCCG</u><br>AGAGGCAGGAGCTTTGGACTCGGGAGGCCGCAGTGAAGCAACAGCTAG<br>CTGGGCGTGGAGAGTCCGCTGTGAGGCAGAGGCTGGGCCTGTGCAGGC<br>CTTCGGGAGGCAGGAGGCTGGGCCTTGTCGAGGCCTGCAGAGGCCACC<br>GAAAGTCAAAAGCGGGGCTTGGGAAGGCCGCCGGGAGGCATGAGCTGG<br>GCTGGGCCGAAAGAGGCCACTGGGAGGCAGGAGGAGCTGGGCCTGGAG<br>AGGCTGCCAAAAGGCAGGAGCTTCGCCTGAGGATGCCACAGTGAGACA<br>CCATCTGGGTCTGGAGGGTCCACTGTGAGGCAGAGGCTGACCTGTAGA<br>GTCCGACAGTAGACAGAAGTTGGGCAAAAGCCTGATTTGAGGAAGTTT<br>TGGGCTTCAAGAGTCAGCCACGAGGCAGGCACTAGGCCTGGAAATGGC<br>CTCACAGTCATGAGTTGGGCCTAAATGGGCCACTGTGAGGGAGGAGCT<br>GTGCCTGTTGAGGCTGCTGGCAGGCAGGCAGAAATTTGGCCTGGGGCA<br>GCTGCCATGAGGCAAGAGCTGGGCCTGGAAAAAGCCCCTGGGAGGCAA<br>GAGCAGGGCCTGCAGAGGCTGTTCTCAAGTCAAAGCTGGGCCTGTTGA<br>TGCCAC<u>CGGGAAGCAGAAGGTGGGCCTGGAGAGTTTGACTTGAGGAAG<br>TTTTGGGCCTACATTGGCCGCCATGAGCTGGACAGGAACTGGGCCAAA<br>AAAGGCTGTTGTGAGGCAGCAGTTGTGCCTGTAGACCCAGCCAAGAGG<br>AAGAGG</u>TGGGTCTGGAGAAGCCCCATGAGGCAGAGGTTGGGCCTGTA<br>GACGCTGACAGGAGGCAGGAGCTGGGCCTGGACAGGTCAACTTGAGGA<br>GATTTTGGGCCTTCATAGGCCACCAGGAGGCAGTAGTTGGGACTAGAG<br>AGTCTGACTTGAGTAAGTTTTGGGCCCGGAGATGACGTCCTGGGACAG<br>GAGTTGGGCGTGGAGAGGCCACCGTGAGGCATAAGCTGGATGTAGAGA<br>GGCCAGTGTGAGGCAAGACCTGGGCCTGTCTAGGCTGCTGGGAGACAG<br>GCAGGAATCTGGCCAGGGAAGGTTGCCATGAGACAAAAGTTGGGCCTG<br>GAAAGGCCCTTGTGAAGCATGAGCTTGGCCTAAAGAGGCCACTGGGTG<br>GCAGGAGCTGGGTGTGTAGAAGCTGCTGAAAGGTTGGGAGCTTGGCTT<br>GGGGGGTCCACAGTGAGGTAGATGCTGGGCGT-3' |

FIG. 5

| SEQ ID NO. 2<br>hT-For1<br>(primer) | 5'-AGTGGGTCTGGAGAGGCCGACTTG-3' |
|---|---|
| SEQ ID NO. 3<br>hT-Rev1<br>(primer) | 5'-TCAGGCCCATGGGGCTCATTCCT-3' |
| SEQ ID NO. 4<br>hT-Pro1 (probe) | 5'-FAM-TTCTGGGCCCGGAGAGGCCGC-BHQ1-3' |
| SEQ ID NO. 5<br>hT-For2<br>(primer) | 5'-GCAGAAGGTGGGCCTGGAGAGTTTGAC-3' |
| SEQ ID NO. 6<br>hT-Rev2<br>(primer) | 5'-CCTTTTTTGGCCCAGTTCCTGTCCAGC-3' |
| SEQ ID NO. 7<br>hT-Pro2 (probe) | 5'-FAM-GGAAGTTTTGGGCCTACATTGGCCGCCATG-BHQ1-3' |
| SEQ ID NO. 8<br>hT-For3<br>(primer) | 5'-AAGGTGGGCCTGGAGAGTTT-3' |
| SEQ ID NO. 9<br>hT-Rev3<br>(primer) | 5'-CCTTTTTTGGCCCAGTTCCTGT-3' |
| SEQ ID NO. 10<br>hT-Pro3 (probe) | 5'-HEX-AAGTTTTGGGCCTACATTGGCCGC-BHQ1 -3' |
| SEQ ID NO. 11<br>4NS1C Scorpion | 5'-Fam-CGAGCTCAGTTGTGCCTGTAGAGCTCG-dabcyl-C18-<br>ACCTCTTCCTCTTGGCTGGG-3' |
| SEQ ID NO. 12<br>4NS1C primer | 5'-CCGGGAAGCAGAAGGTGG-3' |

METHOD FOR QUANTIFYING HUMAN DNA

This application is a National Stage of PCT/EP2012/052913, filed Feb. 21, 2012 which claims priority to European Application No. 11155164.4, filed Feb. 21, 2011, the disclosures of which are incorporated herein by reference in their entirety.

FIELD OF THE INVENTION

The present invention is in the field of molecular biology, diagnostics, more particularly in the field of analytical and forensic sciences. The invention is further in the field of nucleic acid amplification and quantification, more particularly in the field of DNA quantification in forensics.

The instant application contains a Sequence Listing which has been submitted in ASCII format via EFS-Web and is hereby incorporated by reference in its entirety, Said ASCII copy, created on Aug. 15, 2013, is named 0051_0084US1_Sequence_Listing.txt and is 4943 bytes in size.

BACKGROUND

The determination of the quantity of DNA recovered from forensic samples as well as other samples is a critical step in the over all DNA typing process, but also in the detection of DNA in various other fields of science. A narrow range of input DNA from 0.5 to 2 ng is often needed to produce optimal results with for example multiplex DNA typing kits. Therefore, in order to ensure that a positive result is a positive result and/or a negative result is a negative result due to the absence of DNA, quantification of DNA is of absolute importance. Furthermore, the quality of standards for forensic DNA testing laboratories requires human-specific DNA quantification. This is due to isolation techniques that can recover human DNA as well as bacterial and other exogenous DNA. A number of procedures have been developed to permit quantification of human-specific DNA including start-blot techniques, liquid based hybridization assays and real-time PCR (polymerase chain reaction). Currently, real-time PCR is the dominant technique due to its wide dynamic range and ease of automation.

The modern STR-Kits have become much more sensitive and can obtain good results even using low amounts of DNA. Therefore, there is a desire for a method, kit and nucleic acid region that allows precise and accurate quantification of human DNA even in low concentrated samples. There are certain quantification and detection kits already available, however, these have serious drawbacks. One such kit is the Quantifiler Human Kit (Applied Biosystems) another kit is Quantifiler Duo Kit (Applied Biosystems) another kit is the Plexor HY Real-Time PCR Quantification Kit (Promega). Both the Quantifiler Duo Kit and the Plexor HY Kit target an autosomal and a gonosomal (Y-chromosome) target on the genome.

Drawbacks for the kits: According to LaSalle et al., (Forensic Science International: Genetics, "Analysis of Single and Multi-copy Methods for DNA Quantification by Real-Time Polymerase Chain Reaction") the Quantifier Kits are more accurate in the quantification but have a lower dynamic range as the Plexor HY. The Plexor HY offers a higher dynamic range due to the amplification of a multi-copy target, but a lower accuracy. This lower accuracy can be attributed to the multicopy target. If less than the full set of 20 copies on a genome amplify, because of, for example, instability in the target copy number, than the ratio between the amplification between autosomal and gonosomal (Y) target may vary. The dynamic range of the Plexor HY kit is slightly better than that of the other kit (LaSalle et al., Forensic Science International: Genetics, "Analysis of Single and Multi-copy Methods for DNA Quantification by Real-Time Polymerase Chain Reaction"). In a statistical comparison LaSalle et al. demonstrated a significant difference between the two kits.

Another important parameter in forensics is the degradation grade of the DNA, that has to be analyzed. Since the amplicon size of the Quantifier Human and Plexor HY vary from 62 to 133 base pairs (bp), significant differences might be expected when the kits are applied to degraded DNA.

It should be emphasized that there are currently no official calibration standards or reference materials available especially for the quantification of proteins and nucleic acids (Ellison S L, English C A, Burns M J, Keer J T: Routes to improving the reliability of low level DNA analysis using real-time PCR. BMC Biotechnol 6: 33, 2006). A further problem arises from the pipetting error during the dilution of DNA quantification standards. In addition, long time stability of standards which is sometimes difficult in the case of natural polymers like nucleic acids and proteins must be guaranteed to achieve reproducibility. This is especially important in the case of low amounts of these substances. Furthermore, the manufacturing of reference substances has to be carried out under strict quality control to avoid secondary contaminations.

The Directive 2004/9/EC of THE EUROPEAN PARLIAMENT and of THE COUNCIL of 11 Feb. 2004 on the inspection and verification of good laboratory practice (GLP) (Official Journal of the European Union, Vol. L 50, pp. 28-43, 20 Feb. 2004) states in Part B (Revised guidance for the conduct of test facility inspections and study audits) following inspection and audit criteria for test systems and test and reference substances: "Test systems Purpose: to determine whether adequate procedures exist for the handling and control of the variety of test systems required by the studies undertaken in the facility, for example, chemical and physical systems, cellular and microbic systems, plants or animals ( . . . ). Test and reference substances Purpose: to determine whether the test facility has procedures designed (i) to ensure that the identity, potency, quantity and composition of test and reference substances are in accordance with their specifications, and (ii) to properly receive and store test and reference substances . . . ".

According to DIN EN ISO 9000:2005 certified reference material (CRM) is a reference material, accompanied by a certificate, one or more of whose property values are certified by a procedure that establishes metrological traceability to an accurate realization of the unit in which property values are expressed, and for which each certified value is accompanied by an uncertainty at a stated level of confidence.

Processing of the analytical results into DNA profiles also needs to be carefully controlled, and strict guidelines for the identification of alleles have to be developed and followed, to take account of such things as stutters, artefacts, peak size and morphology, variations in peak ratios, and so on. Three independent scientists, or two scientists and an expert system, are currently used in the UK to confirm the accurate designation of DNA profiles.

A centre piece is the quantification of template DNA. This has so far not been addressed adequately.

SUMMARY OF THE INVENTION

The present invention solves the above identified problem and provides for the following solution as outlined below.

Hence the invention relates to a method for quantifying one or more nucleic acids of a genome in a sample comprising the steps of, (a) amplifying a first nucleic acid to be quantified, (b) determining the amount of said first nucleic acid by comparison of the amount of amplification product from said first nucleic acid with at least one amplification product from a second template nucleic acid, (c) wherein said second template nucleic acid was generated using whole genome amplification and wherein the starting concentration of the second template nucleic acid is known.

Herein, whole genome amplification is also referred to as "WGA". It is the amplification of substantially large parts or substantially most parts or all parts of a particular genome by any of numerous methods, such as with random primers. A non limiting list of methods according to the invention includes the following WGA methods:

The first whole genome amplification methods were described in 1992, and were based on the principles of the polymerase chain reaction. Zhang and coworkers (Zhang, L., et al. Proc. Natl. Acad. Sci. USA, 1992, 89: 5847-5851) developed the primer extension PCR technique (PEP) and Telenius and collaborators (Telenius et al., Genomics. 1992, 13(3):718-25) designed the degenerate oligonucleotide-primed PCR method (DOP-PCR) Zhang et al., 1992).

PEP involves a high number of PCR cycles; using Taq polymerase and 15 base random primers that anneal at a low stringency temperature. The PEP protocol has been improved in different ways DOP-PCR is a method which uses Taq polymerase and semi-degenerate oligonucleotides that bind at a low annealing temperature at approximately one million sites within the human genome. The first cycles are followed by a large number of cycles with a higher annealing temperature, allowing only for the amplification of the fragments that were tagged in the first step.

Multiple displacement amplification (MDA, also known as strand displacement amplification; SDA) is a non-PCR-based isothermal method based on the annealing of random hexamers to denatured DNA, followed by strand-displacement synthesis at constant temperature (Blanco et al., 1989, J. Biol. Chem. 264:8935-40). It has been applied to small genomic DNA samples, leading to the synthesis of high molecular weight DNA with limited sequence representation bias (Lizardi et al., Nature Genetics 1998, 19, 225-232; Dean et al., Proc. Natl. Acad. Sci. U.S.A. 2002, 99, 5261-5266). As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a proofreading activity resulting in error rates 100 times lower than the Taq polymerase.

US 2010/0035232 discloses a further approach and US2004/0209298 discloses further amplification methods.

Herein, human genomic DNA is a sample comprising at least a fraction of human genomic DNA, wherein at least one copy of each human chromosome is present, i.e. in a male individual the male set and for a female individual the female set.

Herein, a male individual is an individual or a cell line that carries a full male chromosome set.

Herein, a female individual is an individual or a cell line that carries a full female chromosome set.

The invention also relates to the use of a nucleic acid amplification mixture generated by whole genome amplification for quantifying a further nucleic acid composition.

And, the invention relates to a kit for quantifying nucleic acids, comprising one more vials with a nucleic acid composition that has been generated by means of whole genome amplification.

As used herein, a kit is a packaged combination optionally including instructions for use of the combination and/or other reactions and components for such use.

DETAILED DESCRIPTION OF THE INVENTION

As outlined above, known means of quantifying DNA by making use of a reference DNA and an amplification method have the drawback that the reference DNA may vary from lot to lot.

The invention addresses the need to be able to define test sensitivity, i.e. the amount of DNA that can be detected reliably.

The invention addresses the need to be able to define the amount of DNA that the laboratory can detect reliably in mixture, wherein there is a presence of another DNA.

The invention addresses the need to be able to define the reproducibility with which the laboratory can detect gender specific loci.

The invention addresses the need to be able to calibrate the reproducibility of, e.g. signal intensity, laboratory equipment, chemicals or enzymes.

It addresses the need to be able to understand the influence of certain PCR inhibitors.

The inventors address the above mentioned needs by providing for a method for quantifying one or more nucleic acids of a genome in a sample comprising the steps of, (a) amplifying a first nucleic acid to be quantified, (b) determining the amount of said first nucleic acid by comparison of the amount of amplification product from said first nucleic acid with at least one amplification product from a second template nucleic acid, (c) wherein said second template nucleic acid was generated using whole genome amplification and wherein the starting concentration of the second template nucleic acid is known.

The amplification method is either a non-isothermal method or an isothermal method.

The non-isothermal amplification method may be selected from the group of polymerase chain reaction (PCR) (Saiki et al. (1985) Science 230:1350), quantitative real-time PCR (rt-PCR), ligase chain reaction (LCR) (Landegren et al. (1988) Science 241:1077-1080). Polymerase chain reaction amplification is preferred.

The isothermal amplification method may be selected from the group of helicase-dependent amplification (HDA) (Vincent et al. (2004) EMBO rep 5(8):795-800), thermostable HDA (tHDA) (An et al. (2005) J Biol Chem 280(32):28952-28958), strand displacement amplification (SDA) (Walker et al. (1992) Nucleic Acids Res 20(7):1691-6), multiple displacement amplification (MDA) (Dean et al. (2002) Proc Natl Acad Sci USA 99(8): 5261-5266), rolling-circle amplification (RCA) (Liu et al. (1996) J Am Chem Soc 118:1587-1594), restriction aided RCA (Wang et al. (2004) Genome Res 14:2357-2366), single primer isothermal amplification (SPIA) (Dafforn et al. (2004) Biotechniques 37(5):854-7), transcription mediated amplification (TMA) (Vuorinen et al. (1995) J Clin Microbiol 33: 1856-1859), nicking enzyme amplification reaction (NEAR) (Maples et al. US2009017453), exponential amplification reaction (EXPAR) (Van Ness et al. (2003) Proc Natl Acad Sci USA 100 (8):4504-4509), loop-mediated isothermal amplification (LAMP) (Notomi et al. (2000) Nucleic Acids Res 28(12): e63), recombinase polymerase amplification (RPA) (Piepenburg et al. (2006) PloS Biol 4(7):1115-1120), nucleic acid sequence based amplification (NASBA) (Kievits et al. (1991) J Virol Methods 35:273-286), smart-amplification process (SMAP) (Mitani et al. (2007) Nat Methods 4(3):257-62).

By "isothermal amplification reaction" in context of the present invention it is meant that the temperature does not significantly change during the reaction. In a preferred embodiment the temperature of the isothermal amplification reaction does not deviate by more than 10° C., preferably by not more than 5° C., even more preferably not more than 2° C. during the main enzymatic reaction step where amplification takes place.

Depending on the method of isothermal amplification of nucleic acids different enzymes are required for the amplification reaction. Known isothermal methods for amplification of nucleic acids are the above mentioned, wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and/or nucleases.

"Helicases" are known by those skilled in the art. They are proteins that move directionally along a nucleic acid phosphodiester backbone, separating two annealed nucleic acid strands (e.g. DNA, RNA, or RNA-DNA hybrid) using energy derived from hydrolysis of NTPs or dNTPs. Based on the presence of defined helicase motifs, it is possible to attribute a helicase activity to a given protein. The skilled artisan is able to select suited enzymes with helicase activity for the use in a method according to the present invention. In a preferred embodiment the helicase is selected from the group comprising helicases from different families: superfamily I helicases (e.g. dda, perA, F-plasmid tral protein helicase, uvrD), superfamily II helicases (e.g. recQ, NS3-helicase), superfamily III helicases (e.g. AAV rep Helicase), helicases from DnaB-like superfamily (e.g. T7 phage helicase) or helicases from Rho-like superfamily.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

In one embodiment the nucleic acid sequences of the first nucleic acid and second template nucleic acid stem from the same organism.

In one embodiment the nucleic acids are DNA.

In one embodiment the nucleic acid sequences of the first and second template nucleic acid are of human origin and genomic DNA.

Human genomic DNA is a sample comprising at least a fraction of human genomic DNA. Said sample may additionally comprise other biomolecules such as proteins, mitochondrial DNA or lipids but is ideally free of such biomolecules. In a preferred embodiment the human genomic DNA is isolated from a tissue or a cell line and is in soluble form in water or in a buffer system. However the human genomic DNA may also be lyophilized when starting the WGA amplification. It is important that the respective individual has a normal chromosomal set including all chromosomes.

In a preferred embodiment said second template nucleic acid stems from a nucleic acid mixture from various individuals of a given organism or various human individuals. These can be humans, e.g. male and female or only male or only female. Other sources are also possible. Genomic DNA is preferred.

Ideally, said second template nucleic acid was generated using two or more rounds of whole genome amplification.

Preferably, the comparison is done with two or more amplification products from said second template nucleic acid, wherein the two or more amplification products are generated from different starting concentrations of said second template nucleic acids.

For example, using real-time PCR techniques, fluorescence is detected and measured in the real-time PCR thermocycler, and its geometric increase corresponding to exponential increase of the product is used to determine the threshold cycle ($C_T$) in each reaction. The unknown and each of the standards (amplification product form a second nucleic acid; the WGA DNA) are amplified in separate tubes. A standard curve (plot of $C_T$ value/crossing point against log of amount of standard) is generated using different dilutions of the standard. The $C_T$ value of the unknown samples is compared with the standard curve, allowing calculation of the initial amount of the target. It is important to select an appropriate standard for the type of nucleic acid to be quantified. To generate a standard curve, ideally at least 5 different amounts of the standard should be quantified, and the amount of unknown target should fall within the range of the standard curve. Hence, in one embodiment also the above quantification steps are performed.

Hence, and preferably, the different starting concentrations of said second template nucleic acid have been adjusted in such a way that they reflect a substantially linear range of concentrations.

In one embodiment the second template nucleic acid comprises primarily human nucleic acid sequences and its origin is selected from one of the following tissue types or cell culture types respectively, blood, whole blood, or fractions of blood or isolated nucleated blood cells, buccal swabs, saliva, sputum, urine, other human sample types like biopsies, or other parts of the human body upon availability for isolation of DNA.

In the case of forensic DNA amplification assays a representative set of DNA sources of non human origin can be used to exclude and/or document cross reactivity (see table 1). Hence, in one embodiment, these are the source of the first and second nucleic acid. This may include DNA from phylogenetically closely related species like primates as well as farm animals and pets which live in closeness to men. Non-steril human micro-environments which are sources of forensic DNA samples are skin, mouth (e.g. buccal swabs, sputum), oesophagus, stomach, vagina, gut, colon and faeces. Table 1 includes some major microbial species which are frequently found within samples prepared from healthy persons.

TABLE 1

Collection of species for template DNA.

| Trivial (common) name | Scientific name | Source or location |
|---|---|---|
| horse | *Equus caballus* | farm animal, meat |
| cattle | *Bos taurus* | farm animal, meat |
| cat | *Felis catus* | pet, laboratory animal |
| dog | *Canis lupus familiaris* | pet, laboratory animal |
| mouse | *Mus musculus* | pet, laboratory animal |
| rat | *Rattus norvegicus* | pet, laboratory animal |
| rabbit | *Oryctolagus cuniculus* | farm animal, meat |
| sheep | *Ovis aries* | farm animal, meat |
| golden (Syrian) hamster | *Mesocricetus auratus* | pet, laboratory animal |
| guinea pig | *Cavia aperea* | pet, meat, laboratory animal |
| pig | *Sus scrofa* | farm animal, meat |
| orangutan | *Pongo pygmaeus* | non-human Ape |
| chimpanzee | *Pan troglodytes* | non-human Ape |
| Western gorilla | *Gorilla gorilla* | non-human Ape |
| bonobo | *Pan paniscus* | non-human Ape |
| chicken | *Gallus gallus* | farm animal, meat |
| | *Acinetobacter johnsonii* | human normal skin |
| | *Aspergillus niger* | soil, air |
| | *Bacillus subtilis* | soil, air |
| | *Bacteroides fragilis* | human stool, distal gut |
| | *Bifidobacterium longum* | human stool, distal gut |
| | *Candida albicans* | human skin, vagina |
| | *Corynebacterium tuberculostearicum* | human normal skin |
| | *Corynebacterium coyleiae* | human normal vaginal microflora |
| | *Corynebacterium singulare* | human normal skin |
| | *Enterococcus faecalis* | human normal vaginal, faeces |
| | *Escherichia coli* | human skin, stool |
| | *Finegoldia* AB109769 | human normal skin |
| | *Gemella haemolysans* | human normal oral mricroflora |
| | *Granulicatella adiacens* | human normal oral mricroflora |
| | *Lactobacillus crispatus* | human normal vaginal microflora |
| | *Lactobacillus panis* | human normal vaginal microflora |
| | *Lactobacillus rhamnosus* | human intestine, stool and dairy products |
| | *Methanobrevibacter smithii* | human stool, distal gut |
| | *Neisseria gonorrhoe* | human skin |
| | *Neisseria* spp. | human normal oral mricroflora |
| | *Peptostreptococcus harei* | human normal vaginal microflora |
| | *Peptostreptococcus vaginalis* | human normal vaginal microflora |
| | *Propionibacterium acnes* | human normal skin |
| | *Pseudomonas stuzeri* | human normal skin |
| | *Saccharomyces cerevisiae* | human skin |
| | *Staphylococcus aureus* | human skin, oral flora |
| | *Staphylococcus epidermitis* | human normal vaginal and skin microflora |
| | *Streptococcus mitis* | human normal oral and skin microflora |
| | *Veillionella pravulum* | human normal oral mricroflora |

Microbial type strains deposited at microbial strain collections (e.g. American Type Culture Collections, ATCC; German Collection of Microorganisms and Cell Cultures, DSMZ) or pre-characterized field isolates may be used as sources for the DNA as well. Due to the fact that microbial genomes are 100 (yeast) to 1000 fold (bacteria) smaller than mammalian once, less DNA amounts are needed. Typically, DNA amounts which are equivalent to at least 105 genome copies per PCR are sufficient. In some embodiments mixtures of defined DNA samples from microbials are used within one reaction vessel to safe reagents. DNA from these may also be used.

The region amplified from the second nucleic acid template (the WGA generated template) is ideally a region in SEQ ID NO. 1. The inventors have astonishingly found that this sequence and/or sequences that share sequence similarity with it may be found many times in the human genome. Hence, ideally primers and/or probes are used that bind this sequence.

The sequences distributed throughout the genome are not all exactly identical. It is important that the selected primers bind also to the nearly identical sequences. Thus, ideally the locus shares at least 60%, 70%, 80%, 90% or even 95% or 98% sequence identity to a sequence according to SEQ ID NO. 1 over a stretch of 80 base pairs.

The determination of percent identity between two sequences is accomplished using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program, score=100, word length=12, to obtain nucleotide sequences homologous to SEQ ID NO. 1.

It is an aspect of the invention that multiple copies are amplified from the second WGA generated nucleic acid. Ideally, at least 4, 5, 6, 7, 8, 9, 10, 11, 12, 13, 14, 15, 16, 17, 18, 19, 20, 21, 22, 23, 24, 25, 26, 27, 28, 29 copies on various chromosomes are amplified. SEQ ID NO. 1 or sequences very similar thereto are present 29 times in the human genome. This is not just astonishing but provides for the power of the present method. Also, the copies may be found on various chromosomes such as 1, 4, 5, 7, 11, 16.

The primers ideally used for amplification have a nucleotide sequence that differs from SEQ ID NO. 2, 3, 5, 6, 8, 9, 10, 11 and 12 by no more than 5 nucleotides over a stretch of 18 nucleotides.

Oligonucleotide primers may be prepared using any suitable method, such as, for example, the phosphotriester and phosphodiester methods or automated embodiments thereof. In one such automated embodiment diethyl phosphoramidites are used as starting materials and may be synthesized as described by Beaucage et al. (1981) Tetrahedron Letters 22:1859-1862. One method for synthesizing oligonucleotides on a modified solid support is described in U.S. Pat. No. 4,458,006. It is also possible to use a primer, which has been isolated from a biological source (such as a restriction endonuclease digest). Preferred primers have a length of about 6-100 bases, more preferably about 20-50, most preferably about 20-40 bases.

Additionally, the amplification reaction of the first nucleic acid to be amplified may in one embodiment comprise an internal control (IC) nucleic acid.

The invention also relates to the use of a nucleic acid amplification mixture generated by whole genome amplification for quantifying a further nucleic acid composition.

First or second nucleic acid may comprise an inhibitor which has been added. Inhibitors of PCR are a serious problem in forensic case work. Although a variety of efficient DNA extraction and purification kits is commercially available which efficiently remove proteinaceous inhibitors (e.g. heparin) some water-soluble compounds may overcome the purification steps. Furthermore, analysis of forensic stains with low amounts of DNA requires the concentration of DNA extracts from a huge amount of sample material. Wilson gives an overview of inhibitors (Wilson I G. Inhibition and Facilitation of Nucleic Acid Amplification, Appl Environ Microbiol 63, pp. 3741-3751, 1997). Water-soluble model substances can be used as standards for validation purposes. The following compounds are preferred according to the invention: A potent mixture of inhibitors which is extracted from soil or other environmental sample is humic acid (CAS registry number 1415-93-6); hemin (chloro [3,7,12,17-tetramethyl-8,13-divinylporphyrin-2,18-dipropanoato(2-)] iron (III)) (CAS registry number 14875-96-8) or haematin (CAS registry number 15489-90-4) are degradation products of haemoglobin derived from blood samples. Indigo carmine (CAS registry number 860-22-0) resembles the colour of cotton jeans. Bile salts (equimolar mixture of sodium salts of cholic acid and desoxycholic acid) are water soluble extracts of faeces. Other examples are known to those who are skilled in the art.

Extracts of natural and synthetic products or mixtures thereof are attractive inhibitors, too. For example hot aqueous extracts (boiling in deionized water for 20 min, supernatant after centrifugation at 12,000×g for 10 min at room temperature) of cigarette ash or newspapers (inhibition by printing ink) can be standardized for validation purposes.

For producing the kit according to the invention it may be necessary to stabilise the DNA and the other components. This is done with trehalose, saccharose, glycerin, polymers such as ficoll, dextran, polyvinylpyrolidon, polyacrylamide, other substances such as prolin, ectoin, betain, trimethylammoniumchlorid.

FIGURE CAPTIONS

FIG. 1

Shows data obtained from an experiment with a quantitative real-time PCR using the DNA isolated from Leucocytes (Leuco DNA) and the WGA DNA. In this experiment, a primer and a scorpion primer specific for human DNA were used to amplify a 146 bp fragment of a region present on multiple autosomes (named 4NS1C) (Seq-ID #13 and Seq ID #14). An internal control was coamplified in the same reaction, with primer and scorpions labelled with a distinguishable dye. The Ct value remained constant for all conditions, demonstrating the success of the reaction and no inhibition present. Data for the IC assay are shown in FIG. 2.

Figure 1:
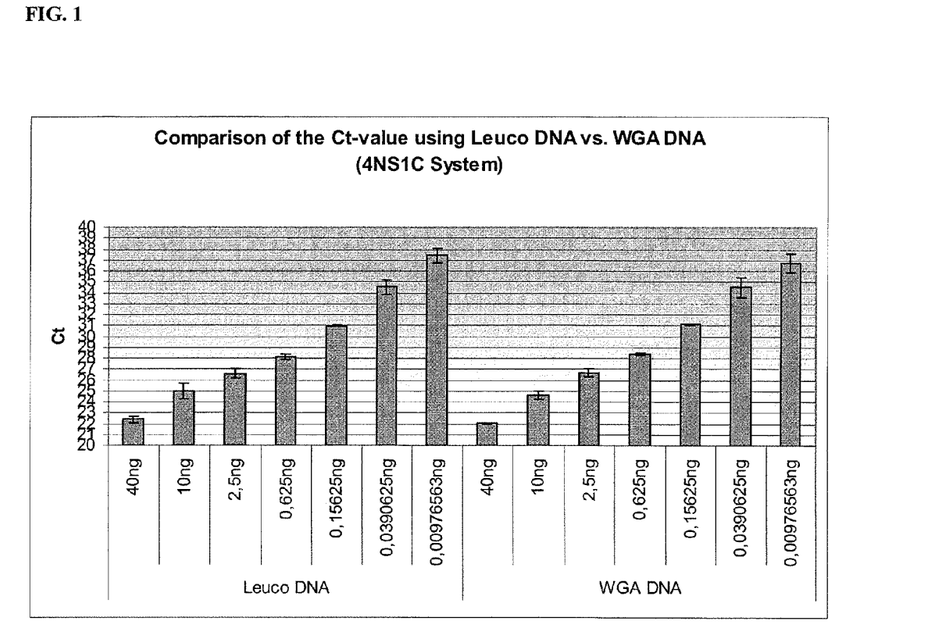
Figure 2:
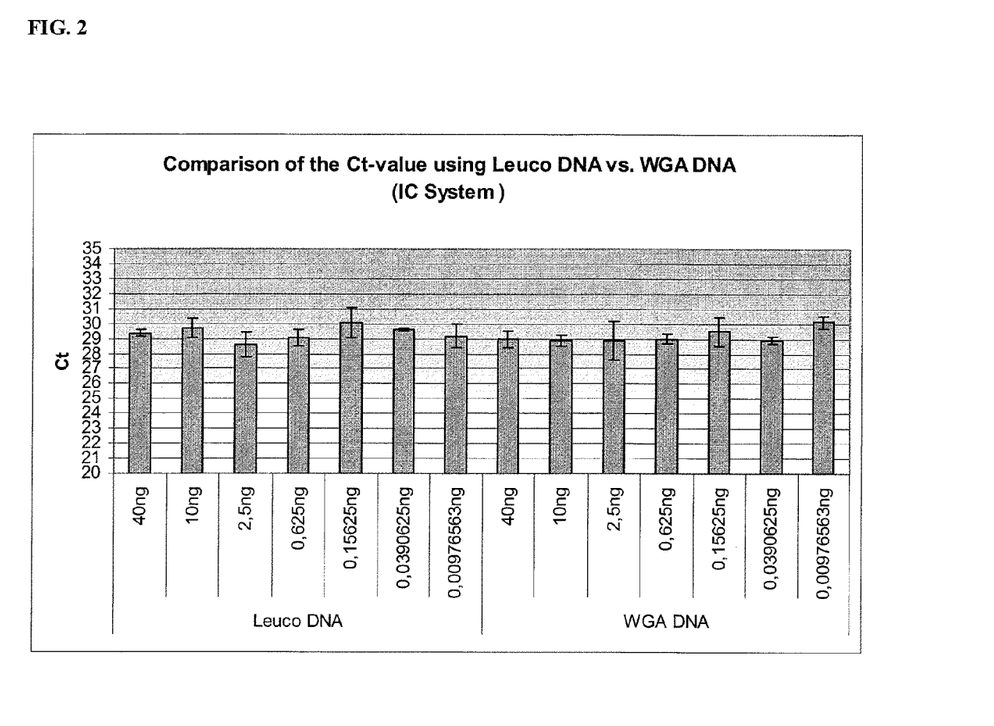

Surprisingly, the CT-values of the 4NS1C target using the Leuco DNA or the WGA DNA are highly similar. This result shows the reliability of WGA for amplifying high quantities of DNA for using in DNA quantification assays.

FIG. 2

Shows data for the internal control coamplified in the same reaction in the setup shown in FIG. 1, with primer and scorpions labelled with a distinguishable dye. In order to check for successful PCR we also added a primer and a scorpion primer specific for an artificial target (named IC or Internal Control). The artificial template for the IC was added in the same concentration in all reaction wells. The CT-values of the IC are not dependent on which template DNA was used for the 4NS1C target, demonstrating the success of the reaction and no inhibition present, and showing suitability of WGA DNA as a quantification standard.

FIG. 3

Shows the data of real-time PCR experiments comparing quantification results for three different methods. In order to test whether WGA DNA is suitable for quantification purposes we used the WGA DNA as standard to quantify the NIST reference material 2372 (human DNA quantitation standard). This standard has an allegedly known concentration (Component A 52.4 ng/µl, Component B 53.6 ng/µl and Component C 54.3 ng/µl). These three components were diluted to the theoretical concentration of 0.25 ng/µl and 0.025 ng/µl. These DNA solutions were then quantified using the WGA DNA as a standard by using a quantitative real-time PCR experiment with an amplification reaction composition comprising, (i) Tris-HCl at a pH of between 8 and 8.8 (at 20° C.) and/or, (ii) potassium salt selected from the group of, potassium chloride and potassium sulphate and/or, (iii) an ammonium salt, preferably ammonium chloride or ammonium sulphate and/or, (vi) magnesium chloride and/or, (v) a hot-start polymerase and (vi) the oligonucleotides with SEQ ID NO. 13 and SEQ ID NO. 14 the inventors showed that the DNA obtained by WGA is a good substitute for human DNA.

Figure 3:
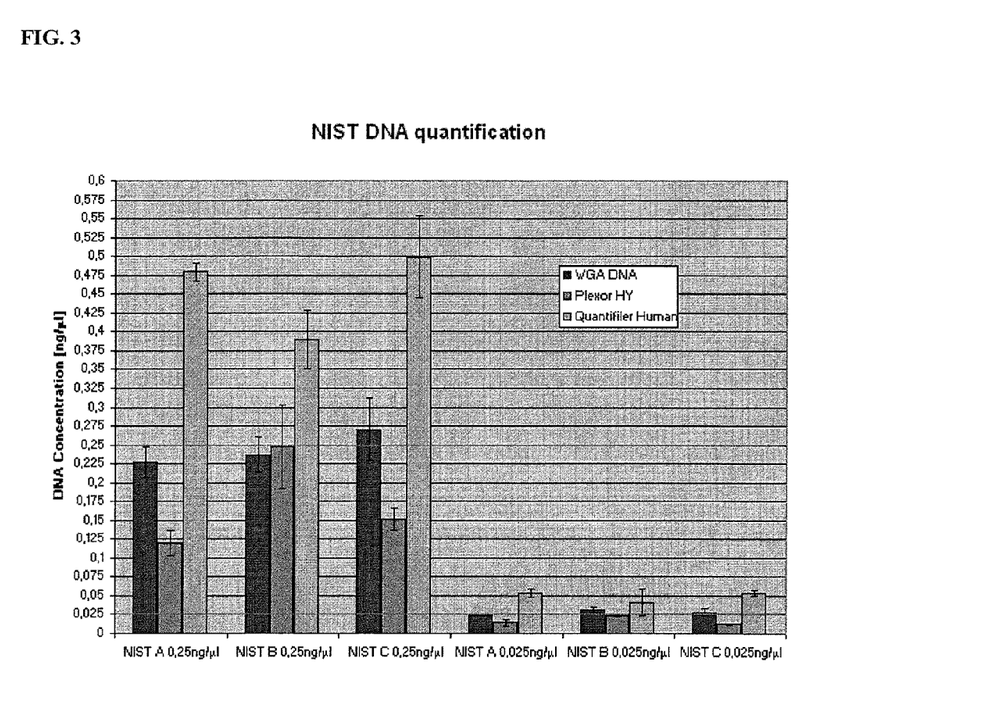
Figure 5:
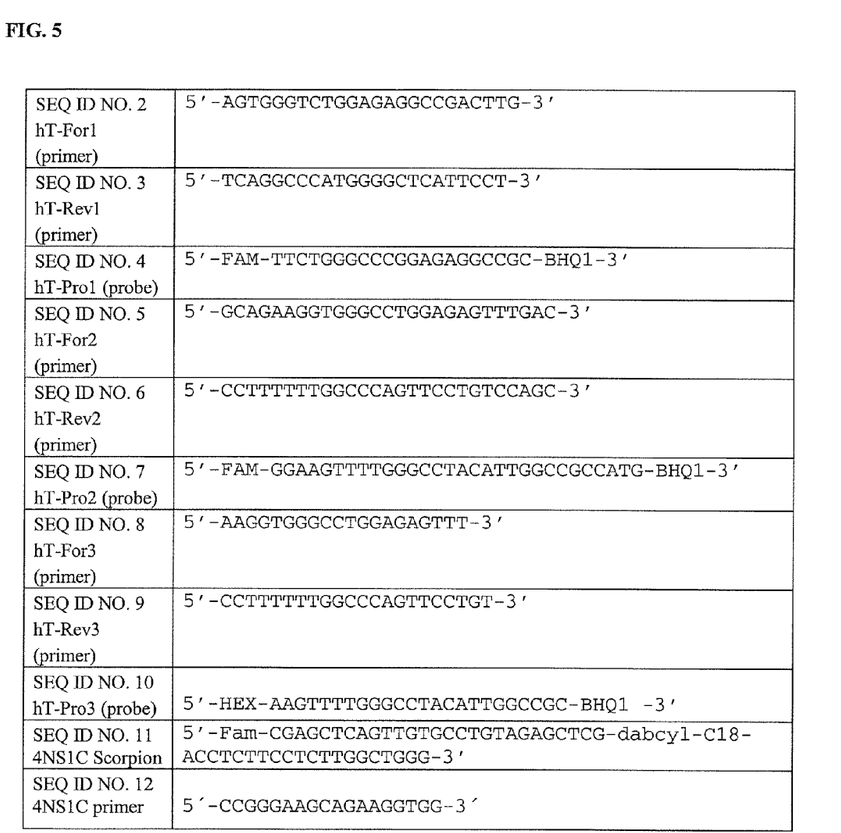

The measured concentrations are also reported in Table 1. All measured concentrations are within the range of ±25% of the theoretical concentration, this error lies within the normal ranges for real-time qPCR. Standard curves were run in duplicates, Test samples (the NIST DNA dilutions) were run in triplicates.

For comparison, accuracy of quantification was also determined using commercially available real-time PCR based DNA quantification kits, the Plexor HY kit from Promega and the Quantifier Human from Applied Biosystems. For both kits, the control DNA coming with the kit was used as quantification standard and the kit used according to the supplied manual. The same dilutions for the NIST DNAs A, B, and C as above were used as unknown Test samples and quantification results were calculated and are shown in FIG. 3. It becomes obvious, that the WGA DNA provides at least as accurate quantification results as the conventional DNA controls coming with the two kits. The obtained quantification values for the NIST DNA avary by up to +/−50% from the theoretical value for both methods, the Plexor HY and the Quantifier Human, but not for the WGA method.

FIG. 4

Target Sequences for the oligonucleotides given. The first underlined region is the Ht target, the second is the 4NS1C target.

FIG. 5

Table with Oligonucleotide sequences

EXAMPLES

The quantification of DNA may be performed using different techniques; herein in one example real-time PCR was added. Different commercial kits are available for this purpose. Especially in the forensic field the quantification of human DNA using real-time PCR is a common method.

Of course, the quality of the control DNA, used for the standard curve in the quantification, has a big influence on the quantification result. The problem with control DNAs in currently available commercial kits is the high variability between different lots. Our solution of the problem is to use WGA (whole genome amplification) to amplify a mixture of human DNAs in order to reduce the variability and provide constant results over a long period of time.

In a quantitative real-time PCR experiment using an amplification reaction composition comprising, (i) Tris-HCl at a pH of between 8 and 8.8 (at 20° C.) and/or, (ii) potassium salt selected from the group of, potassium chloride and potassium sulphate and/or, (iii) an ammonium salt, preferably ammonium chloride or ammonium sulphate and/or, (vi) magnesium chloride and/or, (v) a hot-start polymerase and (vi) the oligonucleotides with SEQ ID NO. 11 and SEQ ID NO. 12 the inventors showed that the DNA obtained by WGA is a good substitute for human DNA.

In the given example, Human DNA from Promega (Cat. Nr. G3041) was used as a template for two rounds of WGA (the product of the first WGA was used as a template for a second WGA). The WGAs were carried out using the REPLI-g Midi Kit following manufacturer's guidelines. The purification after each WGA step was carried out using the QIAamp DNA Blood Maxi Kits following manufacturer's guidelines.

After DNA purification, the obtained quantity of WGA DNA was measured with a photometer (A260). This WGA DNA was compared to a DNA isolated from human leucocytes (QIAamp DNA Blod Kit, Qiagen).

As shown in the experiment below (FIG. 1), the result of a duplex quantitative real-time PCR using the DNA isolated from leucocytes (Leuco DNA) and the WGA DNA was compared. In this experiment, a primer and a scorpion primer specific for human DNA were used to amplify a 146 bp fragment of a region present on multiple autosomes (named 4NS1C/SEQ ID NO. 1; see FIG. 4). In order to check for successful PCR we also added a primer and a scorpion primer specific for an artificial target (named IC or Internal Control). The artificial template for the IC was added in the same concentration in all reaction wells. The Ct-values of the IC are not dependent on which template DNA was used for the 4NS1C target.

```
4NS1C Primer    5'-CCGGGAAGCAGAAGGTGG-3'
(SEQ ID NO. 12)

4NS1C Scorpion  5'-Fam-CGAGCTCAGTTGTGCCTGTAGAGCTCG-
(SEQ ID NO. 11) dabcyl-C18-ACCTCTTCCTCTTGGCTGGG-3'
```

Surprisingly, the Ct-values of the 4NS1C target using the Leuco DNA or the WGA DNA are highly similar (FIG. 1). This result shows the reliability of WGA for amplifying high quantities of DNA for using in DNA quantification assays.

When isolating the DNA from natural samples (buccal swabs, blood, etc) the obtained yield using different methods varies. The typical yield for DNA isolation from healthy whole blood is approximately 4-12 µg using 200 µl blood (source QIAamp DNA Blood Mini Kit). The WGA—typical DNA yields per 50 µl reaction are up to 10 µg (Mini Kit) using 1 to 10 ng of template DNA (source REPLI-g Mini Kit). That means that performing WGA the overall yield of DNA isolation using 200 µl blood can be enhanced over a factor of at least 10,000 from 12 µg to 120,000 µg DNA with a constant DNA quality.

The great advantage of WGA DNA is therefore the possibility to produce big lots of a DNA template with a stable and very constant quality for several years.

The highly stable quality of the control DNA in DNA quantification assays will be a great advantage for scientists using this assay, since current limitations of fluctuations in quality and quantity from production lot to production lot is eliminated (http://marketing.appliedbiosystems.com/images/enews/ForensicNews_Vol5/PDF/01_WhatsNew_Letter.pdf)

In order to test whether WGA DNA is suitable for quantification purposes we used the WGA DNA as standard to quantify the NIST reference material 2372 (human DNA quantitation standard) (see FIG. 3). This standard has an allegedly known concentration (Component A 52.4 ng/µl, Component B 53.6 ng/µl and Component C 54.3 ng/µl). These three components were diluted to the theoretical concentration of 0.25 ng/µl and 0.025 ng/µl. These DNA solutions were then quantified using the WGA DNA as a standard. The measured concentrations are reported in Table 1. All measured concentrations are within the range of ±25% of the theoretical concentration, this error lies within the normal ranges for real-time qPCR. For comparison, accuracy of quantification was also determined using commercially available real-time PCR based DNA quantification kits (see FIG. 3), the Plexor HY kit from Promega and the Quantifier Human from Applied Biosystems. For both kits, the control DNA coming with the kit was used as quantification standard and the kit used according to the supplied manual. The same dilutions for the NIST DNAs A, B, and C as above were used as unknown Test samples and quantification results were calculated and are shown in FIG. 3. It becomes obvious, that the WGA DNA provides at least as accurate quantification results as the conventional DNA controls coming with the two kits. The obtained quantification values for the NIST DNA avary by up to +/−50% from the theoretical value for both methods, the Plexor HY and the Quantifier Human, but not for the WGA method.

TABLE 1

| | Measured concentrations | | | | | |
|---|---|---|---|---|---|---|
| | theoretical concentration [ng/µl] | measured concentration [ng/µl] | Standard Deviation | theoretical concentration [ng/µl] | measured concentration [ng/µl] | Standard Deviation |
| Component A | 0.25 | 0.227443 | 0.020820265 | 0.025 | 0.0245599 | 0.001413008 |
| Component B | 0.25 | 0.236829333 | 0.022564614 | 0.025 | 0.031362133 | 0.003076462 |
| Component C | 0.25 | 0.270458 | 0.041526476 | 0.025 | 0.028518267 | 0.005086746 |

The invention claimed is:

1. Method for quantifying one or more nucleic acids of a genome in a sample comprising the steps of,
   a. amplifying a first nucleic acid to be quantified from a first template nucleic acid,
   b. determining the amount of said first nucleic acid by comparison of the amount of a first amplification product from said first nucleic acid with at least one second amplification product from a second template nucleic acid,
   c. wherein said second template nucleic acid was generated using whole genome amplification and wherein the starting concentration of the second template nucleic acid is known; and
   wherein the second amplification product comprises a sequence at least 60% identical to SEQ ID NO: 1 over a stretch of 80 contiguous base pairs.

2. Method according to claim 1, wherein the nucleic acid sequences of the first nucleic acid and second template nucleic acid are from the same organism.

3. Method according to claim 1, wherein the nucleic acids are DNA.

4. Method according to claim 1, wherein the nucleic acid sequences of the first and second template nucleic acid are of human origin.

5. Method according to claim 1, wherein said second template nucleic acid is from a nucleic acid mixture from various individuals of a given type of organism.

6. Method according to claim 1, wherein said second template nucleic acid was generated using two or more rounds of whole genome amplification.

7. Method according to claim 1, wherein the comparison is done with two or more second amplification products from said second template nucleic acids, wherein the two or more second amplification products are generated from different starting concentrations of said second template nucleic acids.

8. Method according to claim 7, wherein the different starting concentrations of said second template nucleic acid have been adjusted in such a way that they reflect a substantially linear range of concentrations.

9. Method according to claim 1, wherein the second template nucleic acid comprises primarily human nucleic acid sequences and its origin is selected from one of the following samples: blood, whole blood, fractions of blood, isolated nucleated blood cells, buccal swabs, saliva, sputum, urine and biopsies.

10. Method according to claim 1, wherein the amplification reaction of the first nucleic acid to be amplified comprises an internal control nucleic acid.

11. Method according to claim 1, wherein the amplification process is a real-time amplification process.

12. Method according to claim 11, wherein a Ct value is obtained from the real-time amplification process and is compared with a standard curve generated using different dilutions of the second template nucleic acid.

13. The method of claim 1, wherein the second amplification product comprises a sequence at least 70% identical to SEQ ID NO: 1 over a stretch of 80 contiguous base pairs.

14. The method of claim 1, wherein the second amplification product comprises a sequence at least 80% identical to SEQ ID NO: 1 over a stretch of 80 contiguous base pairs.

15. The method of claim 1, wherein the second amplification product comprises a sequence at least 90% identical to SEQ ID NO: 1 over a stretch of 80 contiguous base pairs.

16. The method of claim 1, wherein the second amplification product comprises a sequence at least 95% identical to SEQ ID NO: 1 over a stretch of 80 contiguous base pairs.

17. The method of claim 1, wherein the second amplification product comprises a sequence at least 98% identical to SEQ ID NO: 1 over a stretch of 80 contiguous base pairs.

18. The method of claim 1 wherein the sequence is SEQ ID NO: 1.

19. The method of claim 1, wherein the sequence at least 60% identical to SEQ ID NO: 1 over a stretch of 80 contiguous base pairs is present in at least 10 copies in the second template nucleic acid.

20. The method of claim 1, wherein the sequence at least 60% identical to SEQ ID NO: 1 over a stretch of 80 contiguous base pairs is present in at least 20 copies in the second template nucleic acid.

21. The method of claim 1, wherein the sequence at least 60% identical to SEQ ID NO: 1 over a stretch of 80 contiguous base pairs is present in at least 29 copies in the second template nucleic acid.

22. The method of claim 1, wherein the sequence at least 60% identical to SEQ ID NO: 1 over a stretch of 80 contiguous base pairs is present on a human chromosome selected from the group consisting of chromosomes 1, 4, 5, 7, 11 and 16.

23. The method of claim 1, wherein a primer is used to amplify the sequence at least 60% identical to SEQ ID NO: 1 over a stretch of 80 contiguous base pairs and wherein the primer is selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 10, SEQ ID NO: 11 and SEQ ID NO: 12.

24. The method of claim 1, wherein a primer is used to amplify the sequence at least 60% identical to SEQ ID NO: 1 over a stretch of 80 contiguous base pairs and wherein the primer differs from a polynucleotide selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 10, SEQ ID NO: 11 and SEQ ID NO: 12; by no more than 5 nucleotides over a stretch of 18 contiguous nucleotides.

25. The method of claim 1, wherein two primers are used to amplify the sequence at least 60% identical to SEQ ID NO: 1 over a stretch of 80 contiguous base pairs and wherein the primers are SEQ ID NO: 11 and SEQ ID NO: 12.

* * * * *

SEQUENCE LISTING

<160> NUMBER OF SEQ ID NOS: 12

<210> SEQ ID NO 1
<211> LENGTH: 2000
<212> TYPE: DNA
<213> ORGANISM: Homo sapiens

<400> SEQUENCE: 1

| | | | | | | |
|---|---|---|---|---|---|---:|
| tcaacaggcc | accgtgaggg | aggagctggg | ccgcacgcgg | gctgctggga | ggcaggcagg | 60 |
| gacttggccc | cgagaggccg | ccgtgggggc | aagagctggg | cctggagagg | cccctgggag | 120 |
| gcaagggcgg | ggcctgcaga | ggctgttctc | caaccagtgc | tagaactgta | caggccacca | 180 |
| ggaggcagga | ggtgggccct | cagagcttgg | ctggagaaag | ttcggggcct | acaaaggcgg | 240 |
| ttgggagctg | ggcaggagtt | gagccaaaag | agcttgctta | cttgctggga | ggcagggccg | 300 |
| ggagagcccg | acttcaggac | aacttggggc | tgcggcagtc | gccgggaggc | ccaaccttgg | 360 |
| cgtggaggag | cccaccgacc | ggagaccatt | tggggcctgg | agatgccatc | ggagggcagg | 420 |
| agctcatcct | ggagaggcca | ccgtgaggcc | tgacctgggc | ctggggagct | tggcttgagg | 480 |
| aagctgtggg | ccgaccaagg | ccgccaggag | atgggtaggc | actgagtcca | aagaggttgt | 540 |
| tgagaggcag | gaatcgggcc | tggagaccca | accaggaaga | agagctgggc | ccggagagaa | 600 |
| tgcacggagg | gtgcaagtgg | gtctggagag | gccgacttga | ggaggttctg | ggcccggaga | 660 |
| ggccgccgga | agggaaaaac | tgggcctgga | aaggccgttg | tcaggaatga | gccccatggg | 720 |
| cctgaagagg | ccactggcag | gcgggagctg | ggcctgccga | agcggccgag | aggcaggagc | 780 |
| tttggactcg | ggaggccgca | gtgaagcaac | agctagctgg | gcgtggagag | tccgctgtga | 840 |
| ggcagaggct | gggcctgtgc | aggccttcgg | gaggcaggag | gctgggcctt | gtcgaggcct | 900 |
| gcagaggcca | ccgaaagtca | aaagcggggc | ttgggaaggc | cgccgggagg | catgagctgg | 960 |
| gctgggccga | aagaggccac | tgggaggcag | gaggagctgg | gcctgagag | gctgccaaaa | 1020 |
| ggcaggagct | tcgcctgagg | atgccacagt | gagacaccat | ctgggtctgg | agggtccact | 1080 |
| gtgaggcaga | ggctgacctg | tagagtccga | cagtagacag | aagttgggca | aaagcctgat | 1140 |
| ttgaggaagt | tttgggcttc | aagagtcagc | cacgaggcag | gcactaggcc | tggaaatggc | 1200 |
| ctcacagtca | tgagttgggc | ctaaatgggc | cactgtgagg | gaggagctgt | gcctgttgag | 1260 |
| gctgctggca | ggcaggcaga | aatttggcct | ggggcagctg | ccatgaggca | agagctgggc | 1320 |
| ctggaaaaag | cccctgggag | gcaagagcag | ggcctgcaga | ggctgttctc | aagtcaaagc | 1380 |
| tgggcctgtt | gatgccaccg | ggaagcagaa | ggtgggcctg | gagagtttga | cttgaggaag | 1440 |
| ttttgggcct | acattggccg | ccatgagctg | gacaggaact | gggccaaaaa | aggctgttgt | 1500 |
| gaggcagcag | ttgtgcctgt | agacccagcc | aagaggaaga | ggtgggtctg | gagaagcccc | 1560 |
| catgaggcag | aggttgggcc | tgtagacgct | gacaggaggc | aggagctggg | cctggacagg | 1620 |
| tcaacttgag | gagattttgg | gccttcatag | gccaccagga | ggcagtagtt | gggactagag | 1680 |
| agtctgactt | gagtaagttt | tgggcccgga | gatgacgtcc | tgggacagga | gttgggcgtg | 1740 |
| gagaggccac | cgtgaggcat | aagctggatg | tagagaggcc | agtgtgaggc | aagacctggg | 1800 |
| cctgtctagg | ctgctgggag | acaggcagga | atctggccag | ggaaggttgc | catgagacaa | 1860 |
| aagttgggcc | tggaaaggcc | cttgtgaagc | atgagcttgg | cctaaagagg | ccactgggtg | 1920 |
| gcaggagctg | ggtgtgtaga | agctgctgaa | aggttgggag | cttggcttgg | ggggtccaca | 1980 |
| gtgaggtaga | tgctgggcgt | | | | | 2000 |

```
<210> SEQ ID NO 2
<211> LENGTH: 24
<212> TYPE: DNA
<213> ORGANISM: Artificial Sequence
<220> FEATURE:
<223> OTHER INFORMATION: hT-For1 primer

<400> SEQUENCE: 2
agtgggtctg gagaggccga cttg                                          24

<210> SEQ ID NO 3
<211> LENGTH: 23
<212> TYPE: DNA
<213> ORGANISM: Artificial Sequence
<220> FEATURE:
<223> OTHER INFORMATION: hT-Rev1, primer

<400> SEQUENCE: 3
tcaggcccat ggggctcatt cct                                           23

<210> SEQ ID NO 4
<211> LENGTH: 21
<212> TYPE: DNA
<213> ORGANISM: Artificial Sequence
<220> FEATURE:
<223> OTHER INFORMATION: hT-Pro1 probe

<400> SEQUENCE: 4
ttctgggccc ggagaggccg c                                             21

<210> SEQ ID NO 5
<211> LENGTH: 27
<212> TYPE: DNA
<213> ORGANISM: Artificial Sequence
<220> FEATURE:
<223> OTHER INFORMATION: HT-For2 primer

<400> SEQUENCE: 5
gcagaaggtg ggcctggaga gtttgac                                       27

<210> SEQ ID NO 6
<211> LENGTH: 27
<212> TYPE: DNA
<213> ORGANISM: Artificial Sequence
<220> FEATURE:
<223> OTHER INFORMATION: hT-Rev2 primer

<400> SEQUENCE: 6
ccttttttgg cccagttcct gtccagc                                       27

<210> SEQ ID NO 7
<211> LENGTH: 30
<212> TYPE: DNA
<213> ORGANISM: Artificial Sequence
<220> FEATURE:
<223> OTHER INFORMATION: hT-Pro2 probe

<400> SEQUENCE: 7
ggaagttttg ggcctacatt ggccgccatg                                    30

<210> SEQ ID NO 8
<211> LENGTH: 20
<212> TYPE: DNA
<213> ORGANISM: Artificial Sequence
<220> FEATURE:
<223> OTHER INFORMATION: hT-For3 primer
```

```
<400> SEQUENCE: 8
aaggtgggcc tggagagttt                                              20

<210> SEQ ID NO 9
<211> LENGTH: 22
<212> TYPE: DNA
<213> ORGANISM: Artificial Sequence
<220> FEATURE:
<223> OTHER INFORMATION: hT-Rev3 primer

<400> SEQUENCE: 9 cctttttttgg cccagttcct gt                                          22

<210> SEQ ID NO 10
<211> LENGTH: 24
<212> TYPE: DNA
<213> ORGANISM: Artificial Sequence
<220> FEATURE:
<223> OTHER INFORMATION: hT-Pro3, probe

<400> SEQUENCE: 10
aagttttggg cctacattgg ccgc                                         24

<210> SEQ ID NO 11
<211> LENGTH: 47
<212> TYPE: DNA
<213> ORGANISM: Artificial Sequence
<220> FEATURE:
<223> OTHER INFORMATION: 4NS1C Scorpion

<400> SEQUENCE: 11
cgagctcagt tgtgcctgta gagctcgacc tcttcctctt ggctggg                47

<210> SEQ ID NO 12
<211> LENGTH: 18
<212> TYPE: DNA
<213> ORGANISM: Artificial Sequence
<220> FEATURE:
<223> OTHER INFORMATION: 4NS1C primer

<400> SEQUENCE: 12
ccgggaagca gaaggtgg                                                18
```